United States Patent
Koseoglu

(10) Patent No.: US 10,641,759 B2
(45) Date of Patent: May 5, 2020

(54) PRE-PROCESSING CHARACTERIZATION OF RESIDUAL OIL

(71) Applicant: Saudi Arabian Oil Company, Dhahran (SA)

(72) Inventor: Omer Refa Koseoglu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 594 days.

(21) Appl. No.: 15/397,891

(22) Filed: Jan. 4, 2017

(65) Prior Publication Data

US 2017/0192126 A1   Jul. 6, 2017

Related U.S. Application Data

(60) Provisional application No. 62/275,014, filed on Jan. 5, 2016.

(51) Int. Cl.
*G01N 33/28* (2006.01)
*C10G 9/00* (2006.01)
*C10B 55/00* (2006.01)
*C10B 57/04* (2006.01)

(52) U.S. Cl.
CPC ......... *G01N 33/2823* (2013.01); *C10G 9/005* (2013.01); *C10B 55/00* (2013.01); *C10B 57/045* (2013.01)

(58) Field of Classification Search
CPC .. G01N 33/2823; C10G 9/005; C10B 57/045; C10B 55/00
See application file for complete search history.

(56) References Cited

U.S. PATENT DOCUMENTS

2014/0156241 A1* 6/2014 Kumar ............... G01N 33/2823 703/6

OTHER PUBLICATIONS

Munoz et al, Comparison of Correlations for Estimating Product Yields from Delayed Coking, Energy Fuels 2013, 27, 7179-7190 (Year: 2013).*
The American Petroleum Institute, Petroleum HPV Testing Group, Petroleum Coke Category Analysis and Hazard Characterization (Year: 2007).*

* cited by examiner

*Primary Examiner* — Randy Boyer
*Assistant Examiner* — Juan C Valencia
(74) *Attorney, Agent, or Firm* — Abelman, Frayne & Schwab

(57) ABSTRACT

A system and a method for calculating the coke, gas, and distillate yields that could be derived from residual oil if it were to be subjected to processing methods such as delayed coking, hydroprocessing, gasification, solvent deasphalting, and fluid catalytic cracking, without first performing those processing methods.

6 Claims, 4 Drawing Sheets

PRE-PROCESSING CHARACTERIZATION OF RESIDUAL OIL

CLAIM FOR PRIORITY

This application claims priority to and incorporates by reference U.S. Provisional Patent Application No. 62/275,014, filed on 5 Jan. 2016.

FIELD OF THE INVENTION

This invention relates to a method and process for evaluating a sample of residual oil to determine the coke, gas, and distillate yields that could be derived from the residual oil if it were to be subjected to processing methods such as delayed coking, hydroprocessing, gasification, solvent deasphalting, and fluid catalytic cracking.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

Common crude oil fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

Exhausted oil fields may still contain low concentrations of oil known as residual oil. Residual oil can also be found naturally in fields not previously worked. Residual oil is often mixed with water, and it cannot be recovered conventional techniques. While residual oil fractions that boil above 350° C. contain heavy polynuclear aromatic hydrocarbons, they can nevertheless be converted into valuable products by processing techniques such as delayed coking, hydroprocessing, gasification, solvent deasphalting, and fluid catalytic cracking. For example, delayed coking technology is used to process heavy residual oils to reject carbon as a coke and to recover light fractions as a result of cracking paraffinic side chains and naphthenic rings. The carbon produced in delayed coking technology has three grades: fuel, anode, and needle grades.

Traditionally, the values of products recovered from delayed coking, including coke, gas, and distillates, could only be determined after processing. Due to the processing required and the number of analyses involved, the delayed coking and assay work-up is both costly and time consuming.

This invention discloses a system and method in which the assay values of the coke, gas, and distillates that could be derived from residual oils is actually calculated directly from the residual oil, without first requiring delayed coking or other processing. The invention will help producers, refiners, and marketers to benchmark the quality of the products and, as a result, valuate the products without first going thru costly and time consuming processing and oil assays. Whereas a conventional delayed coking processing and assay could take up to two months, this invention provides results within one hour.

SUMMARY OF THE INVENTION

This invention presents systems and methods for analyzing a residual oil stream to determine coke, gas, and distillate yields that could be obtained from the stream if it were to be processed by a method such as delayed coking. The residual oil stream is directly analyzed to determine the carbon residue value, and then the coke, gas, and distillate yields are calculated as a function of the micro carbon residue.

BRIEF DESCRIPTION OF THE DRAWINGS

Further advantages and features of the present invention will become apparent from the following detailed description of the invention when considered with reference to the accompanying drawings in which.

DETAILED DESCRIPTION OF INVENTION

A system and a method are provided for analyzing a residual oil stream to determine coke, gas, and distillate yields that could be obtained from the stream if it were to be processed by a method such as delayed coking. The calculated yields provide an objective basis for relative evaluation of the residual stream. This helps producers, refiners, and marketers to benchmark the oil quality and, as a result, evaluate the residual oil without performing the customary extensive and time-consuming processing and assaying techniques.

The systems and methods are applicable for residual oil streams boiling above 350° C.

In the system and method herein, carbon residue is determined directly from the residual oil feedstock using ASTM D4530-03 (micro) or ASTM D189-05 (Conradson).

Figure 1:
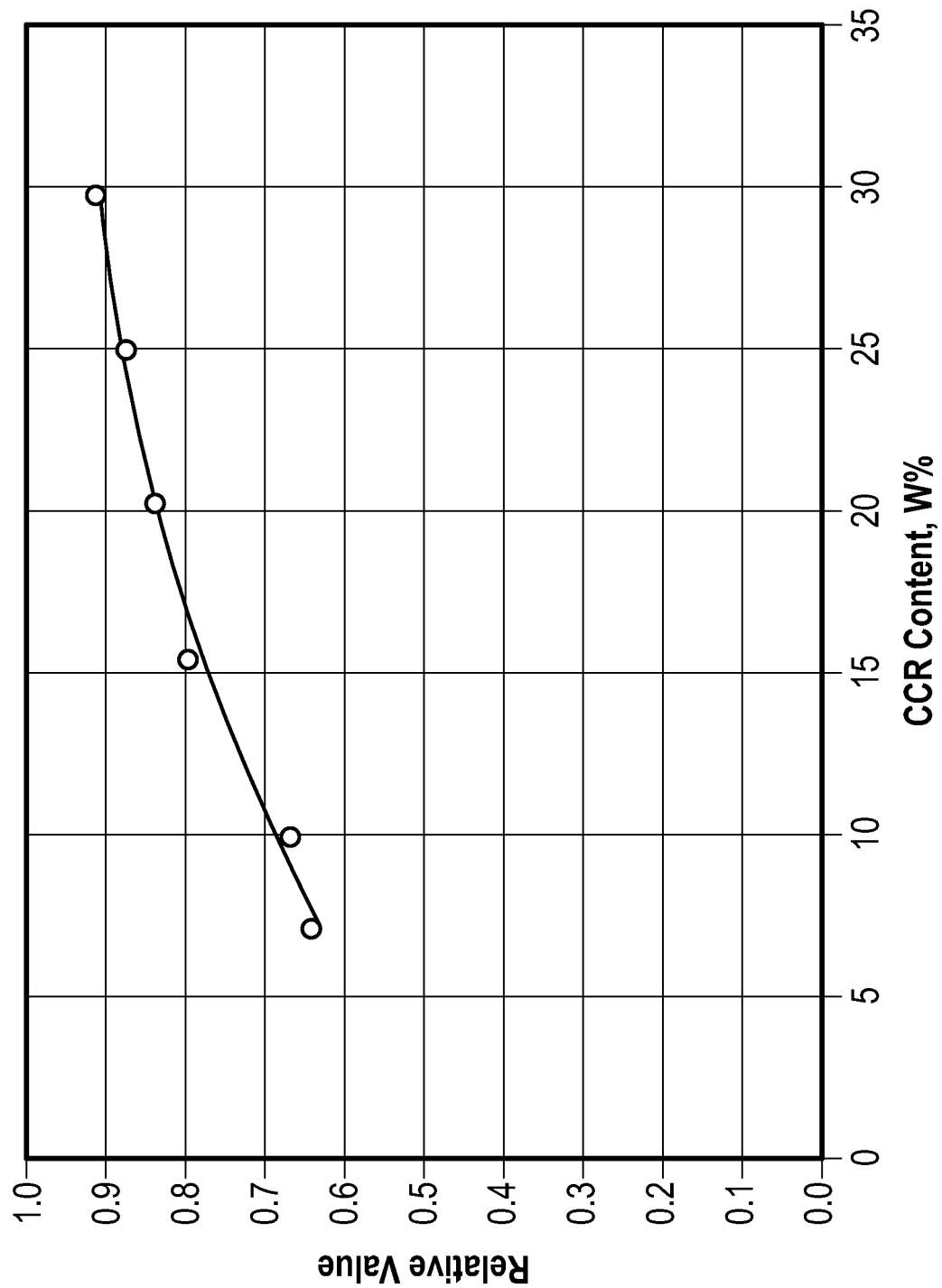
FIG. 1 is a graphic plot displaying relative crude oil prices on the y-axis vs. carbon residue content on the x-axis.

FIG. 1 is a graphic plot displaying relative crude oil prices on the y-axis vs. carbon residue content on the x-axis.

In one embodiment, coke, gas, and distillate yields are calculated from equations 1-5:

$$Y_{Coke}=1.6*CCR \quad (1)$$

$$Y_G=0.144*CCR+7.8 \quad (2)$$

$$Y_N=0.343*CCR+11.29 \quad (3)$$

$$Y_{LCGO}=(100-Y_{Coke}-Y_G-Y_N)*(-0.02273*Y_{Coke}^2+1.193357*Y_{Coke}+45.37)/100 \quad (4)$$

$$Y_{HCGO}=100-Y_{Coke}-Y_G-Y_N-Y_{LCGO} \quad (5)$$

where:

CCR is the Conradson carbon residue, W %;

$Y_{Coke}$ is the coke yield, W %;

$Y_G$ is the gas yield (including methane, ethane, ethylene, propane, propylene, butanes, butylenes, hydrogen sulfide, hydrogen, carbon monoxide, and carbon dioxide);

$Y_N$ is the naphtha yield, W %;

$Y_{LCGO}$ is the light coker gas oil yield, W %;

and $Y_{HCGO}$ is the heavy coker gas oil yield, W %.

The coke, sulfur, and metals contents are calculated from equations 6 and 7:

$$C_{Sulfur}=1.4*F_{Sulfur}+0.18 \quad (6)$$

$$C_{Metals}=100*F_{Metals}/Y_{Coke} \quad (7)$$

where:

$C_{Sulfur}$ is the coke sulfur content, W %;

$C_{Metals}$ is the coke metals (Ni+V) content, ppmw;

$F_{Sulfur}$ is the feedstock sulfur content, W %;

$F_{Metals}$ is the feedstock metals content, ppmw.

If $C_{Metals}$ is less than 650 ppmw and $C_{Sulfur}$ is less than 3.5 W %, then the coke type is suitable for anode. Otherwise, then the coke type is only suitable for fuel.

Following are a number of examples in which a vacuum residue stream has its CCR, feedstock sulfur content and feedstock metals content determined, and then equations 1-7 are applied to determine the coke, gas, and distillate yields, and the coke sulfur content and coke metals content.

Example 1

A vacuum residue stream boiling above 565° C. has an API Gravity of 4.7°, a specific gravity of 1.039, a sulfur W % of 0.37, a metals content of 76 ppmw, and an CCR of 7.1 W %. Applying equations 1-7:

$$Y_{Coke}=1.6*7.1=11.4$$

$$Y_G=0.144*7.1+7.8=8.8$$

$$Y_N=0.343*7.1+11.29=13.7$$

$$Y_{LCGO}=(100-11.4-8.8-13.7)*(-0.02273*11.4^2+1.193357*11.4+45.37)/100=37.0$$

$$Y_{HCGO}=100-11.4-8.8-13.7-37.0=29.0$$

$$C_{Sulfur}=1.4*0.37+0.18=0.70$$

$$C_{Metals}=100*76/11.4=665$$

$C_{Sulfur}$ is less than 3.5 W %, which meets the anode grade coke specification, but $C_{Metals}$ is not less than 650 ppmw, and therefore the coke type is only suitable for fuel.

Example 2

A vacuum residue stream boiling above 565° C. has an API Gravity of 10°, a specific gravity of 1.000, a sulfur W % of 0.75, a metals content of 152 ppmw, and an CCR of 10 W %. Applying equations 1-7:

$$Y_{Coke}=1.6*10=16.0$$

$$Y_G=0.144*10+7.8=9.2$$

$$Y_N=0.343*10+11.29=14.7$$

$$Y_{LCGO}=(100-16.0-9.2-14.7)*(-0.02273*16.0^2+1.193357*16.0+45.37)/100=35.2$$

$$Y_{HCGO}=100-16.0-9.2-14.7-35.2=24.8$$

$$C_{Sulfur}=1.4*0.75+0.18=1.23$$

$$C_{Metals}=100*152/16.0=950$$

$C_{Sulfur}$ is less than 3.5 W %, which meets the anode grade coke specification, but as $C_{Metals}$ is not less than 650 ppmw, the coke type is only suitable for fuel.

Example 3

A vacuum residue stream boiling above 565° C. has an API Gravity of 16.9°, a specific gravity of 0.953, a sulfur W % of 0.14, a metals content of 43 ppmw, and an CCR of 15.4 W %. Applying equations 1-7:

$$Y_{Coke}=1.6*15.4=24.7$$

$$Y_G=0.144*15.4+7.8=10.0$$

$$Y_N=0.343*15.4+11.29=16.6$$

$$Y_{LCGO}=(100-24.7-10.0-16.6)*(-0.02273*24.7^2+1.193357*24.7+45.37)/100=29.7$$

$Y_{HCGO}=100-24.7-10.0-16.6-29.7=19.0$ $C_{Sulfur}=1.4*0.14+0.18=0.38$ $C_{Metals}=100*43/24.7=174$ As $C_{Metals}$ is less than 650 ppmw, and $C_{Sulfur}$ is less than 3.5 W %, the coke type is suitable for anode.

Example 4

A vacuum residue stream boiling above 565° C. has an API Gravity of 7.9°, a specific gravity of 1.015, a sulfur W % of 0.64, a metals content of 41 ppmw, and an CCR of 20.3 W %. Applying equations 1-7:

$Y_{Coke}=1.6*20.3=32.5$ $Y_G=0.144*20.3+7.8=10.7$ $Y_N=0.343*20.3+11.29=18.3$ $Y_{LCGO}=(100-32.5-10.7-18.3)*(-0.02273*32.5^2+1.193357*32.5+45.37)/100=23.2$ $Y_{HCGO}=100-32.5-10.7-18.3-23.2=15.4$ $C_{Sulfur}=1.4*0.64+0.18=1.08$ $C_{Metals}=100*41/32.5=127$ As $C_{Metals}$ is less than 650 ppmw, and $C_{Sulfur}$ is less than 3.5 W %, the coke type is suitable for anode.

Example 5

A vacuum residue stream boiling above 565° C. has an API Gravity of 6.4°, a specific gravity of 1.026, a sulfur W % of 1.25, a metals content of 62 ppmw, and an CCR of 24.98 W %. Applying equations 1-7:

$Y_{Coke}=1.6*24.98=40.0$ $Y_G=0.144*24.98+7.8=11.4$ $Y_N=0.343*24.98+11.29=19.9$ $Y_{LCGO}=(100-40.0-11.4-19.9)*(-0.02273*40.0^2+1.193357*40.0+45.37)/100=16.3$ $Y_{HCGO}=100-40.0-11.4-19.9-16.3=12.4$ $C_{Sulfur}=1.4*1.25+0.18=1.93$ $C_{Metals}=100*62/40.0=154$ As $C_{Metals}$ is less than 650 ppmw, and $C_{Sulfur}$ is less than 3.5 W %, the coke type is suitable for anode.

Example 6

A vacuum residue stream boiling above 565° C. has an API Gravity of 1.7°, a specific gravity of 1.062, a sulfur W % of 1.78, a metals content of 138 ppmw, and an CCR of 29.69 W %. Applying equations 1-7:

$Y_{Coke}=1.6*29.69=47.5$ $Y_G=0.144*29.69+7.8=12.1$ $Y_N=0.343*29.69+11.29=21.5$ $Y_{LCGO}=(100-47.5-12.1-21.5)*(-0.02273*47.5^2+1.193357*47.5+45.37)/100=9.6$ $Y_{HCGO}=100-47.5-12.1-21.5-9.6=9.3$ $C_{Sulfur}=1.4*1.78+0.18=2.67$ $C_{Metals}=100*138/47.5=291$ As $C_{Metals}$ is less than 650 ppmw, and $C_{Sulfur}$ is less than 3.5 W %, the coke type is suitable for anode.

For each example, the calculated values matched the actual values that were obtained when the vacuum residue streams were actually subjected to delayed coking.

Figure 2:
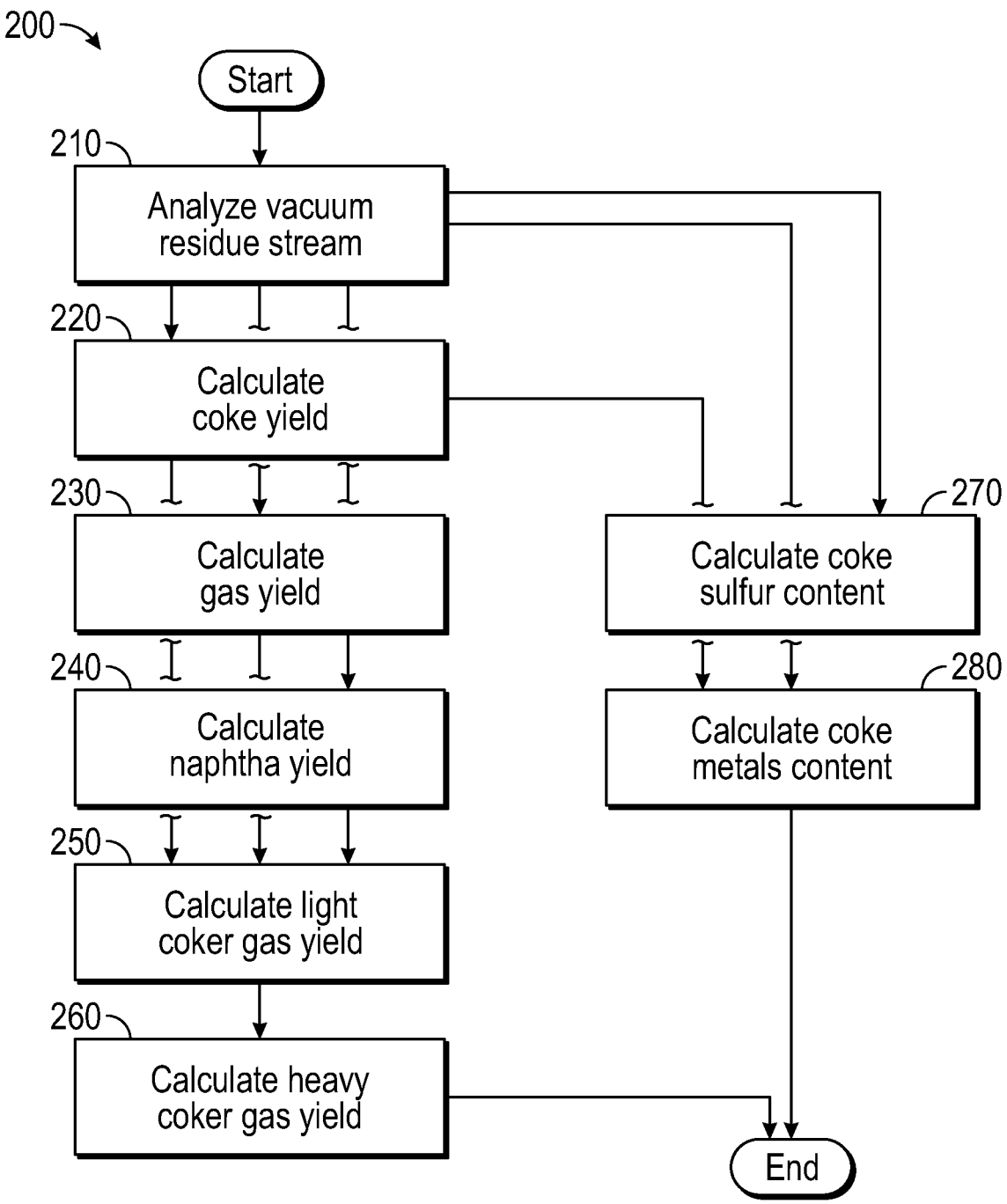
FIG. 2 is a block diagram of a method in which an embodiment of the invention is implemented.

FIG. 2 shows a process flowchart of steps in a method according to one embodiment herein, in which a vacuum residue stream is prepared and analyzed according to the method 200 described below.

In step 210 a sample of a vacuum residue stream is analyzed using ASTM D4530-03 (micro) or ASTM D189-05 (Conradson). The feedstock sulfur content and metals content is also measured.

In step 220, the coke yield that could be expected after delayed coking or comparable processing is calculated.

In step 230, the gas yield that could be expected after delayed coking or comparable processing is calculated.

In step 240, the naphtha yield that could be expected after delayed coking or comparable processing is calculated.

In step 250, the light coker gas yield that could be expected after delayed coking or comparable processing is calculated.

In step 260, the heavy coker gas yield that could be expected after delayed coking or comparable processing is calculated.

In step 270, the coke sulfur content that could be expected after delayed coking or comparable processing is calculated.

In step 280, the coke metals content that could be expected after delayed coking or comparable processing is calculated.

Figure 3:
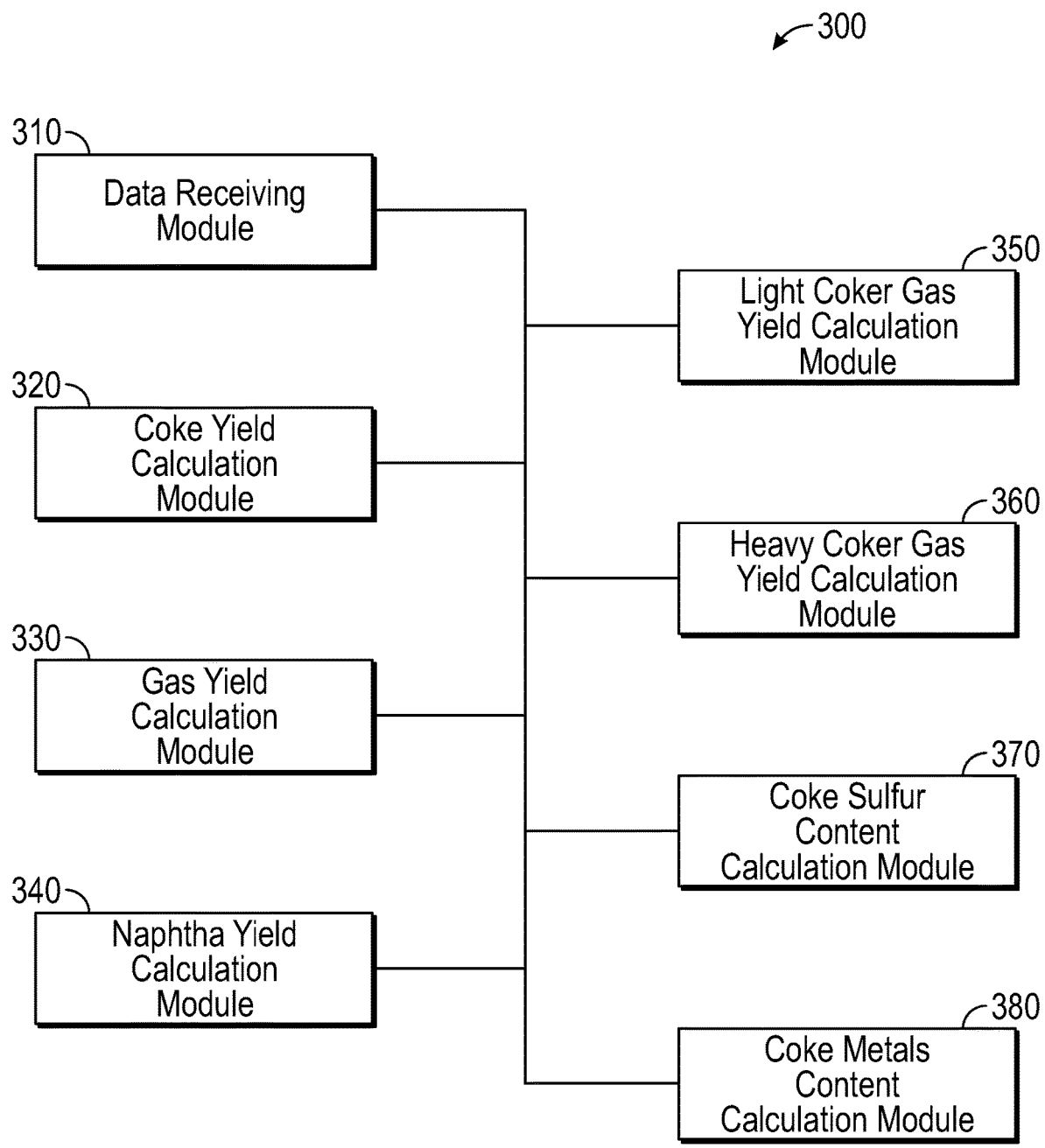
FIG. 3 is a schematic block diagram of modules of an embodiment of the invention.

FIG. 3 illustrates a schematic block diagram of modules in accordance with an embodiment of the present invention, system 300. Data receiving module 310 receives the Conradson carbon residue or micro carbon residue value, together with the values for feedstock sulfur content and metals content.

Coke yield calculation module 320 calculates the coke yield that could be expected after delayed coking or comparable processing.

Gas yield calculation module 330 calculates the gas yield that could be expected after delayed coking or comparable processing.

Naphtha yield calculation module 340 calculates the naphtha yield that could be expected after delayed coking or comparable processing.

Light coker gas yield calculation module 350 calculates the light coker gas yield that could be expected after delayed coking or comparable processing.

Heavy coker gas yield calculation module 360 calculates the heavy coker gas yield that could be expected after delayed coking or comparable processing.

Coke sulfur calculation module 370 calculates the coke sulfur content that could be expected after delayed coking or comparable processing.

Coke metals calculation module 380 calculates the coke metals content that could be expected after delayed coking or comparable processing.

Figure 4:
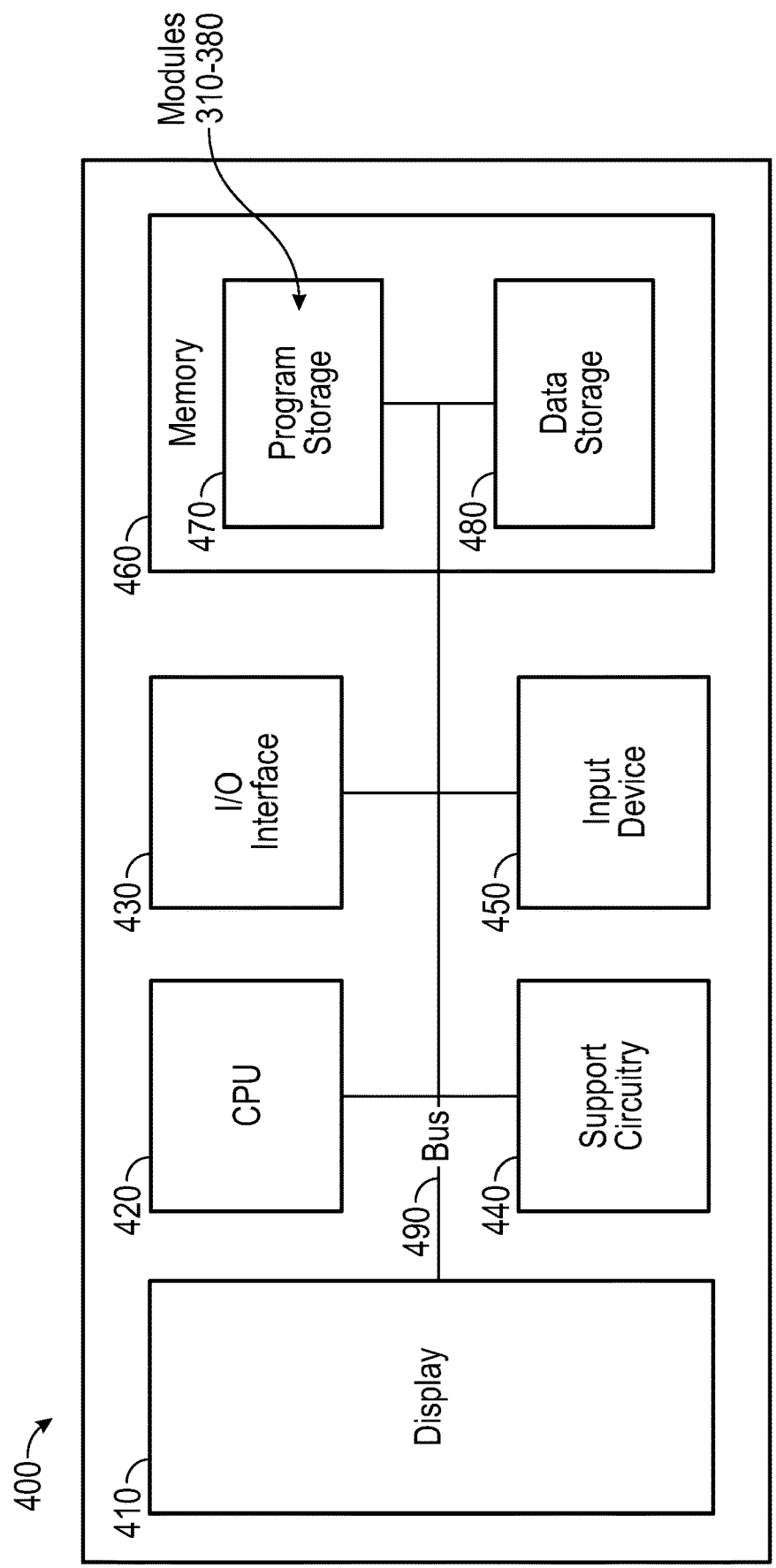
FIG. 4 is a block diagram of a computer system in which an embodiment of the invention is implemented.

FIG. 4 shows an exemplary block diagram of a computer system 400 in which the system of the present invention can be implemented. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data, and in particular stores a data receiving module 310, coke yield calculation module 320, gas yield calculation module 330, naphtha yield calculation module 340, light coker gas yield calculation module 350, heavy coker gas yield calculation module 360, coke sulfur calculation module 370, and coke metals calculation module 380. Data storage memory 480 stores results and other data generated by the one or more modules of the present invention.

It is to be appreciated that the computer system 400 can be any computer such as a personal computer, minicomputer, workstation, mainframe, a dedicated controller such as a programmable logic controller, or a combination thereof. While the computer system 400 is shown, for illustration purposes, as a single computer unit, the system can comprise a group of computers which can be scaled depending on the processing load and database size.

Computer system 400 preferably supports an operating system, for example stored in program storage memory 470 and executed by the processor 420 from volatile memory. According to an embodiment of the invention, the operating system contains instructions for interfacing computer system 400 to the Internet and/or to private networks.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 U.S.P.Q.2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figures; however, modifications will be apparent to those of ordinary skill in the art and the scope of protection for the invention is to be defined by the claims that follow.

I claim:

1. A system for evaluating a sample of a residual oil feedstock and calculating coke, gas, and distillate yields, coke sulfur and metals content, and ranking of coke type that could be derived from the residual oil feedstock if it were to be subjected to delayed coking, without first performing delayed coking, the system comprising:

a non-volatile memory device that stores calculation modules and data, the data including a feedstock sulfur content ($F_{Sulfur}$), a feedstock metals content ($F_{Metals}$), and a carbon residue value of the feedstock sample, where the carbon residue value is selected from one of a Conradson carbon residue value (CCR) or a micro carbon residue value;

a processor coupled to the non-volatile memory;

the non-volatile memory device including a computer readable program code embodied therein as said calculation modules, the computer readable program code adapted to be executed by the processor coupled to the memory to implement a method for calculating the coke, gas, and distillate yields, the coke sulfur and metals content, and the ranking of coke type that could be derived from the residual oil feedstock, the method comprising:

retrieving the carbon residue value from the non-volatile memory, calculating the coke yield ($Y_{Coke}$) as a function of the carbon residue value, and storing the coke yield into the non-volatile memory;

retrieving the carbon residue value from the non-volatile memory, calculating the gas yield ($Y_G$) as a function of the carbon residue value, and storing the gas yield into the non-volatile memory;

retrieving the carbon residue value from the non-volatile memory, calculating naphtha yield ($Y_N$) as a function of the carbon residue value, and storing the naphtha yield into the non-volatile memory;

retrieving the coke yield, gas yield, and naphtha yield from the non-volatile memory, calculating light coker gas oil yield ($Y_{LCGO}$) as a function of the coke yield, gas yield, and naphtha yield, and storing the light coker gas oil yield into the non-volatile memory;

retrieving the coke yield, gas yield, naphtha yield, and light coker gas oil yield from the non-volatile memory, calculating heavy coker gas oil yield ($Y_{HCGO}$) as a function of the coke yield, gas yield, naphtha yield, and light coker gas oil yield, and storing the heavy coker gas oil yield into the non-volatile memory;

retrieving the feedstock sulfur content from the non-volatile memory, calculating the coke sulfur content ($C_{Sulfur}$) as a function of the feedstock sulfur content, and storing the coke sulfur content into the non-volatile memory; and retrieving the feedstock metals content and the coke yield from the non-volatile memory, calculating the coke metal content ($C_{Metals}$) as a function of the feedstock metals content and the coke yield, and storing the coke metal content into the non-volatile memory;

ranking the coke type as suitable for anode if $C_{Metals}$<650 ppmw and $C_{Sulfur}$<3.5 W %, and otherwise ranking the coke type as only suitable for fuel, and storing the ranking into the non-volatile memory.

2. The system of claim 1, wherein the carbon value is the micro carbon residue value, and the residual oil feedstock sample contains a micro carbon residue value in the range of 0.01-50 W %, a sulfur level in the range of 0.01-10 W %, and a metals level in the range of 0.01-2000 ppmw.

3. The system of claim 1, wherein: Calculating the coke yield ($Y_{coke}$) as a function of the carbon residue value uses equation $Y_{coke}$=1.6*carbon residue value;

Calculating the gas yield ($Y_G$) as a function of the carbon residue value uses equation $Y_G$=0.144*carbon residue value+7.8;

Calculating the naphtha yield ($Y_N$) as a function of the carbon residue value uses equation $Y_N$=0.343*carbon residue value+11.29;

Calculating the light coker gas oil ($Y_{LCGO}$) as a function of the coke yield, gas yield, and naphtha yield uses equation $Y_{LCGO}$=(100−$Y_{COKE}$−$Y_G$−$Y_N$)*(−0.02273*$Y_{Coke}^2$+1.193357*$Y_{Coke}$+45.37)/100;

Calculating the heavy coker gas oil yield ($Y_{HCGO}$) as a function of the coke yield, naphtha yield, and light coker gas oil yield uses equation $Y_{HCGO}$=100−$Y_{coke}$−$Y_G$−$Y_N$−$Y_{LCGO}$;

Calculating the coke sulfur content ($C_{sulfur}$) as a function of the feedstock sulfur content uses equation $C_{sulfur}$=1.4*$F_{Sulfur}$+0.18; and Calculating the coke metal content ($C_{Metals}$) as a function of the feedstock metals content and the coke yield uses equation $C_{Metals}$=100*$F_{Metals}$/$Y_{Coke}$.

4. A method for evaluating a sample of a residual oil feedstock and calculating coke, gas, and distillate yields, coke sulfur and metals content, and ranking of coke type that could be derived from the residual oil feedstock if it were to be subjected to delayed coking, without first performing delayed coking, the method comprising:

providing a computer comprising a processor coupled to a non-volatile memory, wherein the non-volatile memory stores calculation modules and data, the data including a feedstock sulfur content ($F_{Sulfur}$), a feedstock metals content ($F_{Metals}$), and a carbon residue value of the feedstock sample, where the carbon residue sample is selected from one of a Conradson carbon residue value (CCR) or a micro carbon residue value;

using the processor to retrieve the carbon residue value from the non-volatile memory, to calculate the coke yield ($Y_{Coke}$) as a function of the carbon residue value, and to store the coke yield into the non-volatile memory;

using the processor to retrieve the carbon residue value from the non-volatile memory, to calculate the gas yield ($Y_G$) as a function of the carbon residue value, and to store the gas yield into the non-volatile memory;

using the processor to retrieve the carbon residue value from the non-volatile memory, to calculate naphtha yield ($Y_N$) as a function of the carbon residue value, and to store the naphtha yield into the non-volatile memory;

using the processor to retrieve the coke yield, gas yield, and naphtha yield from the non-volatile memory, to calculate light coker gas oil yield ($Y_{LCBO}$) as a function of the coke yield, gas yield, and naphtha yield, and to store the light coker gas oil yield into the non-volatile memory; and using the processor to retrieve the coke yield, gas yield, naphtha yield, and light coker gas oil yield from the non-volatile memory, to calculate heavy coker gas oil yield ($Y_{HCGO}$) as a function of the coke yield, gas yield, naphtha yield, and light coker gas oil yield, and to store the heavy coker gas oil yield into the non-volatile memory;

using the processor to retrieve the feedstock sulfur content from the non-volatile memory, to calculate the coke sulfur content ($C_{Sulfur}$) as a function of the feedstock sulfur content, and to store the coke sulfur content into the non-volatile memory;

using the processor to retrieve the feedstock metals content and the coke yield from the non-volatile memory, to calculate the coke metal content ($C_{Metals}$) as a function of the feedstock metals content and the coke yield, and to store the coke metal content into the non-volatile memory; and determining the ranking of the coke type as suitable for anode if $C_{Metals}$<650 ppmw and $C_{Sulfur}$<3.5 W %, while otherwise determining the ranking of the coke type as only suitable for fuel, and storing the ranking into the non-volatile memory.

5. The method of claim 4, wherein the carbon value is the micro carbon residue value, and the residual oil feedstock sample contains a micro carbon residue value in the range of 0.01-50 W %, a sulfur level in the range of 0.01-10 W %, and a metals level in the range of 0.01-2000 ppmw.

6. The method of claim 4, wherein:

$Y_{coke}$=1.6*carbon residue value;

$Y_G$=0.144*carbon residue value+7.8;

$Y_N$=0.343*carbon residue value+11.29;

$Y_{LCGO}$=(100−$Y_{Coke}$−$Y_G$−$Y_N$)*(−0.02273*$Y_{Coke}^2$+1.193357*$Y_{Coke}$+45.37)/100;

$Y_{HCGO}$=100−$Y_{Coke}$−$Y_G$−$Y_N$−$Y_{LCGO}$.

$C_{Sulfur}$=1.4*$F_{Sulfur}$+0.18; and $C_{Metals}$=100*$F_{Metals}$/$Y_{Coke}$.

* * * * *